United States Patent [19]

Stanker et al.

[11] Patent Number: 5,334,528
[45] Date of Patent: Aug. 2, 1994

[54] MONOCLONAL ANTIBODIES TO CYCLODIENE INSECTICIDES AND METHOD FOR DETECTING THE SAME

[75] Inventors: Larry H. Stanker, Livermore; Martin Vanderlaan, Danville; Bruce E. Watkins, Livermore, all of Calif.

[73] Assignee: The Regents of the University of California, Oakland, Calif.

[21] Appl. No.: 428,537

[22] Filed: Oct. 30, 1989

[51] Int. Cl.$^5$ .......................... C12N 5/20; C07K 15/00
[52] U.S. Cl. ................................ 435/240.27; 435/7.9; 436/548; 436/815; 530/388.9
[58] Field of Search .................... 435/71, 70.21, 172.2, 435/948, 28, 188, 240.27; 436/815, 548, 174–178; 530/387, 808, 388.9; 935/103, 105, 110; 210/656, 198.2; 502/407

[56] References Cited

U.S. PATENT DOCUMENTS 4,056,468 11/1977 Breiter et al. .................... 436/178

OTHER PUBLICATIONS

Vanderlaan, J., et al. "Monoclonal Antibodies for the Detection of Trace Chemicals: Pesticide Science and Biotechnology", Proceedings of the 6th International Congress of Pesticide Chemistry; Blackwell Scientific Publications, Oxford, England (1987) pp. 597–602.

Vanderlaan, M., et al. "Environmental Monitoring by Immunoassay" *Environ. Sci. Technol.*, 22(3): 247–254 (1988).

Dreher, R. M. et al, "Development of an Enzyme Immunoassy for Endosulfan and Its Degradation Products" *J. Agric. Food Chem.* 36: 1072–1075 (1988).

Langone et al., Chem Abs 83:2009x. 1975.

Serier et al., Clin. Chem. 27(11), 1797–1806, 1981.

*Primary Examiner*—Esther L. Kepplinger
*Assistant Examiner*—Donna C. Wortman
*Attorney, Agent, or Firm*—Hana Dolezalova

[57] ABSTRACT

Methods are described for making specific monoclonal antibodies useful for detection of cyclodienes in foods and environmental samples. Monoclonal antibodies specifically reactive with cyclodienes can detect accumulated pesticides in food, tissue or environmental samples. Extraction and preparation of organic samples for immunoassay in a polar-nonpolar reaction medium permits detection of halogenated organic ring structures at concentrations in samples.

3 Claims, 4 Drawing Sheets

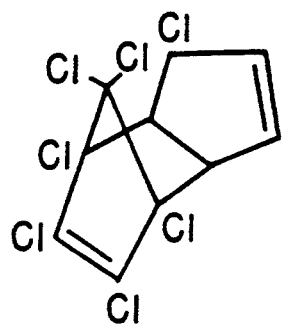
heptachlor
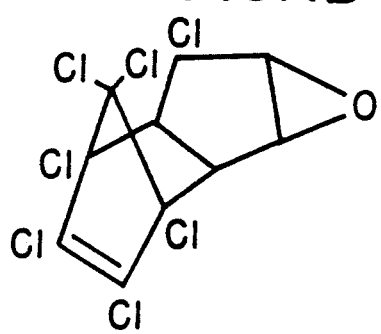
heptachlor epoxide
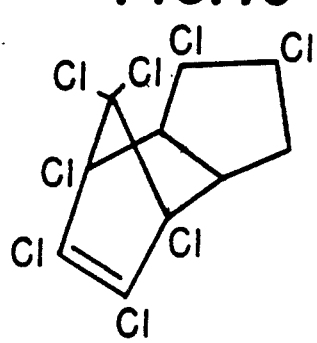
chlordane
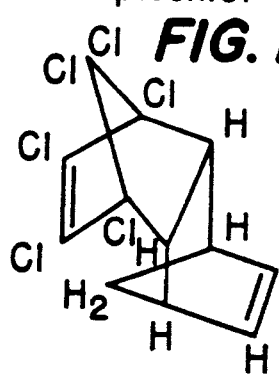
aldrin
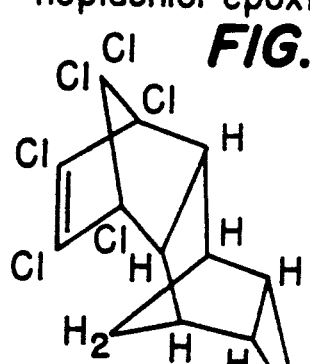
dieldrin
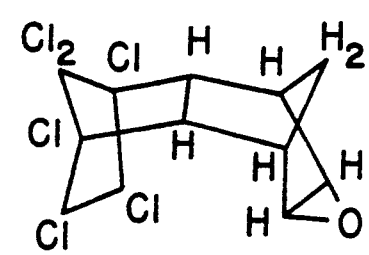
endrin
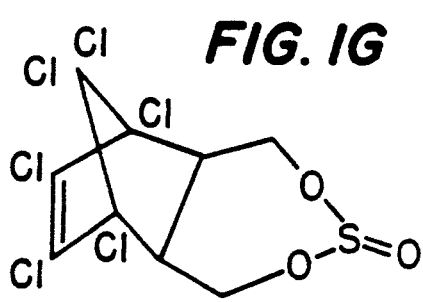
endosulfan
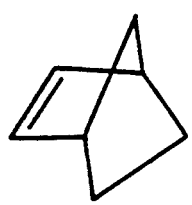
norbornene nucleus cELISA Analysis of Beef Fat Spiked with Heptachlor Heptachlor Analysis by cELISA in Fish

MONOCLONAL ANTIBODIES TO CYCLODIENE INSECTICIDES AND METHOD FOR DETECTING THE SAME

The United States Government has rights in this invention pursuant to Contract No. W-7405-ENG-48 between The Regents of The University of California and the United States Department of Energy.

The subject invention is related generally to assay of insecticides found in foods and environmental samples and more particularly to production and use of monoclonal antibodies for specific detection of cyclodiene insecticides.

IDENTIFICATION OF TERMS

Abbreviations or definitions used in the disclosure herein are as follows:

cELISA: competition enzyme-linked immunosorbent assay.
BSA: bovine serum albumin.
KLH: keyhole limpet hemocyanin.
GC/EC: gas chromatography/electron capture.
GABA: gamma-amino butyric acid, a neurotransmitter which increases the permeability of the post-synaptic membrane to $Cl^-$ ion.
hapten: a small molecule which carries an antigenic determinant, but is not immunogenic until it is chemically coupled to a larger protein carrier. The hapten-carrier complex then stimulates an immune competent cell to form antibodies to the hapten and the complex;
HPLC: high pressure liquid chromatography.
cyclodiene insecticides: chlorinated hydrocarbon insecticides, containing an endomethylene bridge which include heptachlor, chlordane, aldrin, dieldrin, endrin, Strobane®, endosulfan, toxaphene and BHC (mixed isomers) benzene hydrochloride.
heptachlor: 1,-exo-,4,5,6,7,8,8,-Heptachloro-3a,4, 7,7a-tetrahydro-4,7-methanoindene.
heptachlor epoxide: the product of heptachlor oxidation, which occurs in soil, in animals, and in or on crops when treated with heptachlor.
chlordane: 2,3,4,5,6,7,8,8-Octachloro-2,3,3a,4, 7,7a-hexahydro-4,7-methanoindene.
aldrin: 1,2,3,4,10,10-Hexachloro-1,4,4a,5,8,8a hexahydro-1,4-exo, endo-5,8,-dimethanonaphthalene (HHDN).
dieldrin: (1R, 4S, 5S, 8R)-1,2,3,4,10,10-hexachloro-1,4,4a,5,8,8a-5 -hexahydro-1,4:5,8-dimethano-naphthalene (principal constituent, known as HEOD).
endosulfan: 6,7,8,9,10,10-Hexachloro-1,5,5a,6, 9,9a-hexahydro-6,9,-methano-2,4,3-benzo[e]-dioxathiepin-3-oxide.
endrin: (1R, 4S, 5R, 8S) 1,2,3,4,10,10-hexachloro-6,7-epoxy-1,4,4a,5,6,7,8,8a-octahydro-exo-5,8,dimethano-naphthalene.
Strobane®: polychlorinates of camphene, pinene and related terpenes. (Production discontinued by Tenneco Chemicals, Inc.).
norbornene: isomer resulting from the maximal interaction between the unsaturated systems of the reaction between cyclopentadiene and maleic anhydride. The acid anhydride ring system is fused to the newly formed methylene-bridged cyclohexene nucleus (bicyclo[2.2.1]hept-2-ene; norbornene) through its endo positions.
camphene: $C_{10}H_{10}$.
toxaphene: (camphechlor) isomeric reaction mixture of chlorinated camphenes containing 67-69% chlorine.
BHC: 1,2,3,4,5,6-Hexachlorocyclohexane; also known as benzene hexachloride. There are five isomers, of which one, gamma BHC, has insecticidal activity and is known as the pesticide lindane.
Kepone®: Decachloro-octahydro-1,3,4,-metheno-2H-cyclobuta(cd) pentalen-2-one (Discontinued by Allied Chemical Co.).

BACKGROUND OF THE INVENTION

Cyclodiene insecticides are a large group of polychlorinated cyclic hydrocarbons with endomethylene bridged structures. A variety of chlorinated hydrocarbon insecticides were prepared by the Dieis-Alder reaction following the discovery of chlordane in 1945, and various derivatives were widely used in the United States and other countries. Until recent discontinuance of production, or limitations on domestic usage, the cyclodiene insecticides most commonly used in the United States were heptachlor, chlordane, aldrin, dieldrin, endrin, Strobane® endosulfan toxaphene and BHC (FIG. 1).

Cyclodiene insecticides may have one or more 5 or carbon rings which have been heavily halogenated. Cyclodienes may have a single cyclopentadiene ring or a dicyclopentadiene ring structure. The structure of bicyclo[2.2.1]hept-2-ene has a joined pair of five carbon rings, which is formed by the joint sharing of three carbons, and is termed the norbornene functionality. The norbornene structure is a common structure of many cyclodiene insecticides. Cyclodienes may have a dicyclopentadiene ($C_{10}H_{12}$) ring structure in which 3 carbons are shared commonly between two 5 carbon rings and also 2 carbons may be shared commonly between one of those rings and another 5 carbon or substituted five-carbon ring. Each of the ring structures is extensively halogenated, with the ring hydrogens most commonly being replaced with chlorine.

Cyclodiene insecticides act upon the central nervous system by inhibition of ATPase activity which affects ion transport and interferes with nerve cell receptors. The increased level of intracellular $Ca^{+2}$ caused by inhibition of ATPase activity promotes transmitter release at synapses of the central nervous system. Additionally, cyclodiene insecticides, specifically heptachlor epoxide, inhibit $Cl^-$ uptake by neurons by competitive binding to the picrotoxinin receptor of the central nervous system. Inhibition of the $Cl^-$ uptake causes an uncontrolled excitation in cells normally supplied by GABA, gamma-amino butyric acid.

The cyclodiene insecticides in use differ widely in their chemical structure, toxicity and photostability. Historically, heptachlor was heavily used in agriculture as an insecticide and termiticide until these applications were phased out in the mid-1970's. Currently, heptachlor use is restricted, however, previous widespread use of these compounds has led to concern about the possibility that pesticide residues might remain in foodstuffs and the environment. Severe environmental contamination has occurred because the highly lipophilic compounds such as dieldrin and heptachlor epoxide have half-lives in the soil of 2-10 years. Bioaccumulation of these compounds has resulted in their widespread distribution in human fat and milk. Fish have been found with a 100,000-300,000-fold accumulation of these materials from water. These compounds are extremely toxic to fish, birds and small mammals. Cyclodienes have been listed as potentially oncogenic pesticides by the U.S. Environmental Protection Agency. (See Regulating Pesticides in Food: The Delaney Paradox, National Research Council Board on Agriculture, National Academy Press, Washington, D.C., 1987.)

Residues of heptachlor and heptachlor epoxide in meats, fats and milk have been monitored in the United States by the U.S.D.A. Heptachlor epoxide is a major metabolite in body tissue and milk of cows which have grazed on heptachlor-treated pasture. Residue limits for cyclodienes have been set by the U.S. Environmental Protection Agency, the Food and Agricultural Organization and the World Health Organization. However, the lack of convenient, rapid detection systems has hampered environmental identification and quantification of cyclodienes. Conventional analysis for these compounds includes total organic chlorine content or multi-step sample clean-up using organic solvent extraction procedures followed by gas chromatography and electron capture (GC/EC). The complexity of standard chemical extraction and purification of compounds which appear with such low incidence requires other means to rapidly and specifically quantify these materials which are often contaminated with other materials. Specific characterization of the presence and concentration of cyclodienes with cyclodiene-specific antibodies would permit rapid, automatable analysis of these materials in foods and environmental samples.

Monoclonal antibodies have considerable usefulness as diagnostic and therapeutic agents in clinical, commercial and research applications. Refinements of the general technique for hybridoma production developed by Kohler and Milstein in 1975 (*Nature* 256: 495–497) make it possible to produce large quantities of monoclonal antibodies which are able to recognize specific antigenic determinants.

While development of antibodies reactive to protein antigenic sites is repeatable, fabrication of monoclonal antibodies reactive to small organic chemicals, such as carcinogens, pesticides, toxic chemicals and DNA adducts, is less straight-forward. Production of antibodies to such molecules may sometimes be achieved by linking a small molecule, termed a hapten, to a carrier protein prior to immunization of an animal. The immune reactive cells may respond to an antigenic determinant site of this complex, and specifically to (1) the hapten molecule, (2) the carrier protein, (3) the hapten carrier-protein complex, or (4) any combination of the hapten, the linkage chemistry and the carrier protein. The specific reactive site is not known and is unpredictable. The specificity of the antibodies produced may be influenced by the site and chemistry of the hapten conjugation to the carrier protein.

Antibodies with specific binding to reactive sites on small organic molecules are sensitive indicators, which may distinguish chemical isomers (Stanker et al, *Toxicology* 45: 229–243 1987). With small haptens, the greatest antibody specificity for a reactive group appears to occur when that reactive group is most distant from the site of the linkage binding to the carrier protein. Because of distinctive binding features, monoclonal antibodies have greater binding specificity than polyclonal antibodies. Previous attempts at immunization have produced polyclonal antibodies which have poor specificity for heptachlor.

Therefore, there is a need for a specific, sensitive rapid assay for detection of cyclodienes which are found in food and environmental samples. Ideally, such an assay would require minimal sample preparation and be able to detect small amounts of cyclodiene, and be adaptable to field use situations. There is a need for a simple detection system that will recognize several members of the cyclodiene class.

SUMMARY OF THE INVENTION

Accordingly, it is an object of the present invention to provide monoclonal antibodies and the hybridomas that produce such monoclonal antibodies which will react specifically and sensitively with cyclodienes, particularly those antibodies with a high degree of specificity for a class of halogenated hydrocarbons which possess the cyclopentadiene or dicyclopentadiene ring, and more particularly those antibodies with a high degree of specificity for a class of cyclodienes which possess the norbornene structure.

Another object is to provide a method for production of monoclonal antibodies which identify cyclodiene insecticides, particularly those with the cyclopentadiene or dicyclopentadiene functionality, more preferably those with the norbornene structure, and including production of a monoester of heptachlor hapten which will elicit formation of these antibodies.

A further object is to provide a method for the specific and sensitive detection and separation of cyclodiene insecticides from samples, particularly a class of cyclodiene insecticides which possess the cyclopentadiene or dicyclopentadiene functionality, and more particularly a class of cyclodiene insecticides which possess the norborene structure, by binding to specific monoclonal antibodies.

Another object is to provide a method for separation of halogenated cyclic organic compounds from tissue or environmental samples and solubilizing them in a vehicle appropriate for assay of halogenated cyclic organic compounds by specific monoclonal antibodies.

Another object is to provide a method for the detection and isolation of cyclodiene insecticides, particularly those with cyclopentadiene or dicyclopentadiene functionalities, and more particularly those with the norbornene structure, in environmental and food samples.

Additional objects, advantages and novel features of the invention will be set forth in part in the description which follows, and in part will become apparent to those skilled in the art upon examination of the following and the accompanying drawings and their descriptions which form part of the disclosure, or may be learned by practice of the invention. The objects and advantages of the invention may be realized and attained by means of the instrumentalities and combinations particularly pointed out in the appended claims.

To achieve the foregoing and other objects and in accordance with the purpose of the present invention as embodied and broadly described herein, the subject invention is directed to the monoclonal antibody, and the hybridoma which produces it, which is specifically reactive to the cyclodienes which have a cyclopentadiene or dicyclopentadiene functionality, and more specifically, to cyclodiene insecticides which have the norbornene structure. Such compounds include, but are not limited to those shown in Table I, and derivatives thereof. The present invention also provides a method for the production and use of monoclonal antibodies reactive with the antigenic determinants on compounds selected from the group consisting of the cyclodiene insecticides which have a cyclopentadiene or dicyclopentadiene functionality, or more particularly to those with the norbornene structure.

The method for the production of monoclonal antibodies to cyclodiene insecticides in accordance with the subject invention is adapted from general methods for production of monoclonal antibodies, such as that described by Kohler and Milstein (1975), which is incorporated by reference. Cyclodiene-specific antibodies are produced by immunizing a suitable mammal with an immunogenic carrier protein conjugate of the desired antigen compound and obtaining immunosensitized cells from the mammal, which are capable of producing antibodies to the antigen. The immunosensitized cells are fused with immortally reproducing cells of the same species, or of another mammal species. The hybrid cells produced are cultured in a suitable host, or in a culture medium, and clones of hybrid cells, referred to as hybridomas, are isolated. The hybridomas continuously produce specific antibodies which react with the sensitizing antigen and from them cells are selected which produce monoclonal antibodies of desired reactivity. These antibodies are grown in culture medium or in a host, and harvested and purified, if desired.

The monoclonal antibodies produced are capable of recognizing cyclodiene insecticides, particularly those with the cyclopentadiene or dicyclopentadiene functionalities, and more particularly those with norbornene structure. The cell lines developed in accordance with the instant invention are capable of producing highly specific monoclonal antibodies which may be used to distinguish the presence of cyclodiene insecticides in foods and environmental samples. These antibodies are contemplated to be useful for the sensitive detection of cyclodiene insecticides in tissue and surface samples.

The disclosed cyclodiene insecticide specific antibodies produced according to the present method may be used as attachment agents in an affinity column for the concentration and purification of cyclic pesticide structures which may contain substitutions on the ring structure. The subject method of use provides for preparation of samples containing polar soluble compounds so that they may be rapidly and automatically screened for polar compounds, by a nonpolar immunoassay with monoclonal antibodies.

The procedure for isolation of assay samples is suitable for materials found in environmental samples and in common foods. The extraction procedure developed for assay of food or environmental samples by specific monoclonal antibodies may also be used when samples are assayed by GC/EC. A kit format of the diagnostic method may be used for field testing of environmental surface wipe samples.

BRIEF DESCRIPTION OF THE DRAWINGS

FIG. 1A, 1B, 1C, 1D, 1E, 1F, 1G, and 1H show the general chemical structure of some cyclodiene insecticides, specifically outlining the structures for heptachlor, heptachlor epoxide, clordane, aldrin, dieldrin, endrin, endosulfan, and the norbornene ring structure, respectively.

DETAILED DESCRIPTION OF THE INVENTION

Figure 2:
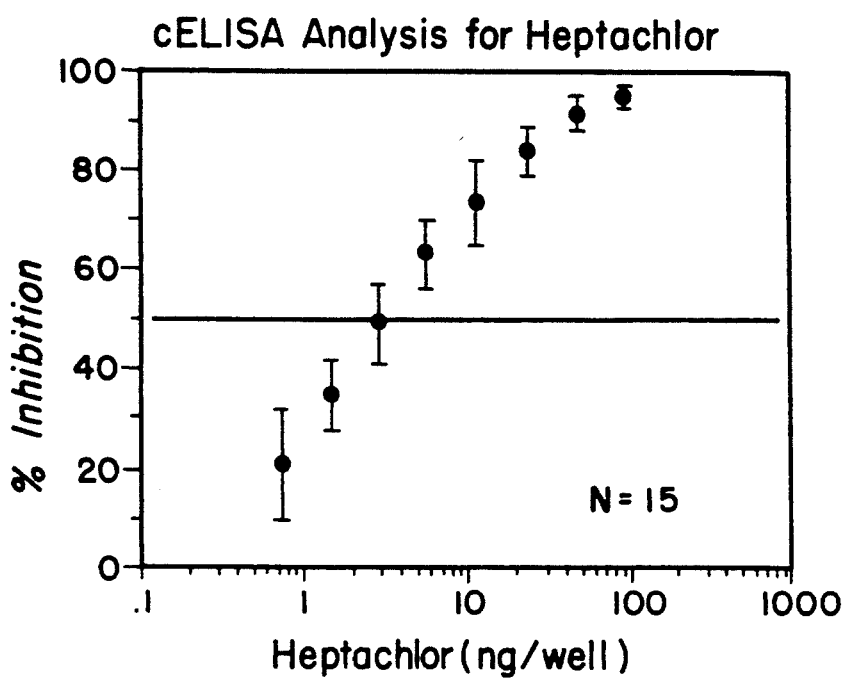
FIG. 2 shows representative competition ELISA data for the monoclonal antibody from hybridoma Hept-2, (closed circles) when heptachlor is used as a competitor Bars represent +/− one standard deviation.

The subject invention is directed to a group of monoclonal antibodies, and the hybridomas which continuously produce them, which react specifically with the described group of cyclodiene insecticides, which contain the cyclopentadiene or dicyclopentadiene ring, and more particularly to those which contain the norbornene structure. The present invention also provides a method for making monoclonal antibodies reactive to chlorinated cyclodiene insecticides with the cyclopentadiene or dicyclopentadiene rings, more particularly to those which contain the norbornene structure. The subject invention provides a method for preparation of samples containing fat-soluble halogenated cyclic organic compounds so that they may be assayed by aqueous-based immunoassay.

Immunogen

Cyclodiene insecticides are small organic molecules, and in order to render them immunogenic, it was necessary to conjugate such molecules to carrier protein by a method such as that described in Stanker et al. in Toxicol. 45: 229-243 (1987), which is incorporated by reference. Various modifications of cyclodienes may be made in an effort to achieve this purpose. In particular, a functional group was introduced into chlordene by which it could be conjugated to a carrier protein. In the preferred example, hexachlorocyclopentadiene and cyclopentadiene are allowed to react together and the resulting intermediate is oxidized to form 1-hydrochlordene. This intermediate was connected with a succinate linker to a carrier protein to form the immunogen. The carrier protein was selected from any of several immunogenic proteins such as keyhole limpet hemocyanin, serum albumins and thyroglobulin. In the preferred mode, the analog hapten of heptachlor was linked through succinate to BSA as the protein conjugate.

Immunization to Raise Antibodies

Techniques for the immunization of laboratory mammals with proteins are known to those skilled in the art. However, when the antigenic compounds are short peptide fragments or small nonproteinaceous molecules, immunization with these compounds may fail to produce an adequate immune reaction. Modified small molecules, termed haptens, may be conjugated to a known immunogen or to a carrier protein which is a known immunogen and by such a linkage be rendered immunogenic. Mammalian antibodies raised in response to an immunogenic conjugate may recognize the small molecule apart from the carrier protein. Carrier proteins may be selected from any of a group of proteins which are immunogenic. Suitable carrier proteins include, but are not limited to, keyhole limpet hemocyanin (KLH), serum albumins, including bovine serum albumin (BSA), globulins including thyroglobulins and the like. Keyhole limpet hemocyanin (KLH) and bovine serum albumin (BSA) are conveniently employed in the subject invention.

The method for the production of monoclonal antibodies which are capable of distinguishing the presence of cyclodiene insecticides with the cyclopentadiene or dicyclopentadiene ring structure and more particularly of distinguishing the presence of cyclodienes with the norbornene structure in accordance with the subject invention, comprises immunizing a suitable mammal, preferably mice, rats, hamsters, rabbits, goats, sheep, cows and horses, still more preferably mice, with an antigen hapten conjugate, preferably with an antigen of heptachlor succinate hapten, which has been conjugated to an immunogenic carrier protein. Repeated intraperitoneal (i.p.) administration of the antigen is made to a first species of mammal in a suitable amount, preferably between about 10 $\mu$g to about 200 $\mu$g, with about 50 $\mu$g (i.p.) per animal, per administration of heptachlor carrier protein conjugate being especially preferred. The antigen may be mixed with adjuvant, preferably Ribi adjuvant (Ribi Immunochemical Research Corp., Hamilton Mont.), and administered at intervals of about two weeks for several, preferably three immunizations.

Immunosensitized spleen cells or lymphocytes, preferably sensitized spleen cells, which are now capable of producing antibodies to the antigen of choice, are removed from the animal. The sensitized spleen cells or lymphocytes are fused with immortally reproducing cells, preferably myeloma cells of the first species of mammal or of another species, to produce hybrid cells. The hybrid cells are cultured in a suitable host or in a culture medium. The clones of hybrid cells, known as hybridomas, which continuously produce or secrete specific antibodies to an antigen of the aforenamed group, are isolated. Hybridomas which produce monoclonal antibodies that distinguish the presence of cyclodienes are selected, quantities of these monoclonal antibodies are generated, antibodies from the culture medium or from the host used for growing the cells are harvested, the monoclonal antibodies isolated and purified, if preferred, and monoclonal antibodies so produced are used to assay samples for the presence of cyclodienes. The hybridomas may be propagated in a suitable host animal or grown in a suitable culture or carrier medium. Host animals are mammals which include, but are not limited to, those described previously. Suitable culture media include, but are not limited to, ascites fluid, hybridoma supernatant or synthetic media, such as D-MEM, RPMI or Iscocos, as well as one of the culture media specified above.

Screening for Antibodies

Antibodies were screened for their ability to bind to the analog hapten of heptachlor-BSA and were also selected for those similarly responsive to the related cyclodiene compounds, heptachlor epoxide, chlordane, aldrin, as well as the synthesized antigen, heptachlor-KLH, but were not responsive to the carrier proteins alone. The selection procedure also included screening for antibody which would be active in the solvent system of the immunoassay. This screening eliminates clones that recognize the linkage chemistry of the conjugate protein. Those clones which test positively with respect to the hapten regardless of carrier protein and negative with respect to the two carrier proteins in the presence of immunoassay solvent were subcloned. Those clones which could recognize free heptachlor, heptachlor epoxide and/or chlordane were evaluated by c-ELISA.

According to a further aspect of the present invention, in accordance with its objects and purposes, the hybridoma cell line, designated as Hept-2, was developed. The clone of said cell line is capable of producing monoclonal antibody of high specificity with which to distinguish the presence of the described cyclodienes with the cyclopentadiene or dicyclopentadiene functionality, more preferably to distinguish the presence of the described cyclodienes with the norbornene structure. This cell line was deposited with the American Type Culture Collection (ATCC), 12301 Parklawn Drive, Rockville, Md. 20852 USA, and has been accorded Accession Number ATCC No. HB 10623 on Dec. 11, 1990.

Deposit Accessability

This hybridoma deposit was made pursuant to a contract between the ATCC and the assignee of this patent application. The contract with the ATCC provides for permanent availability of said strain and progeny thereof to the public upon issuance of a U.S. patent related to this application describing and identifying the deposit or upon the publication or laying open to the public of any U.S. or foreign patent application, whichever comes first, and for the availability of this strain and the progeny thereof to one determined by the U.S. Commissioner of Patents and Trademarks to be entitled thereto according to 35 USC 122 and the Commissioner's rules pursuant thereto (including 37 CFR 1.14 with particular reference to 886 OG 638). The assignee of the present application has agreed that if the strain on deposit should die or be lost or destroyed when cultivated under suitable conditions, it will be promptly replaced upon notification with a viable culture of the same strain.

The depository, under the terms of the Budapest Treaty, assures that said cultures deposited will be maintained in a viable and uncontaminated condition for a period of at least five years after the most recent request for the furnishing of a sample of a deposited hybridoma cell line was received by the ATCC and, in any case, for a period of at least 30 years after the date of the deposit.

Availability of the deposited strain is not to be construed as a license to practice the invention in contravention of the rights granted under the authority of any government in accordance with its patent laws.

Also, the present invention is not to be considered limited in scope by the strain deposited, since the deposited embodiments are intended only to be illustrative of particular aspects of the invention. Any hybridoma cell lines which are functionally equivalent to these deposited are considered to be within the scope of this invention. Further, various modifications of the invention, in addition to those shown and described herein apparent to those skilled in the art from the preceding description, are considered to fall within the scope of the appended claims.

Assay for Cyclodiene Insecticides

Specificity of the antibody is evaluated by a method such as that modified from the direct binding ELISA assay method of Stanker et al. (1986) (*J. Immunol.* 136: 4174–4180), which is incorporated by reference. This assay is run in small reaction volumes, 100 µl, of multiple samples and standards on a plate with 96 reaction wells, termed a microtiter plate.

Antibodies of this invention may be used in the form of hybridoma supernatant, or as ascites fluid, or as the isolated and purified monoclonal antibodies. The sensitivity of the assay is dependent upon the type of binding antigen used to coat the microtiter plate. Any of the several described cyclodiene antigens may be used to coat the microtiter plate, the preferred antigen being a BSA protein conjugate of heptachlor.

The binding specificities of antibodies to standards and assay samples were evaluated by competition ELISA assays. In a competition assay system, an antigen, which is a large molecule with protein or carbohydrate moieties which can precisely bind with steric interaction with the conformation of the antibodies, is fixed to the reaction surface of a test plate. Antigen-specific antibody is added along with an aliquot of sample extract or standard test solution. The free-floating antibody partitions between the fixed antigen bound to the test reaction surface and the antigen of the added sample or standard, which is free-floating in the solution. After a reaction period, the free-floating antigen-antibody complex is washed away. The plate is rewashed and incubated with an enzyme-tagged indicator molecule which will immunospecifically bind to the proteins of the animal species which was the source of the cyclodiene-specific antibodies. Substrate and buffer are provided for the reaction of the enzyme-tagged indicator molecule. The optical signal generated from the enzyme substrate reaction indicates the amount of cyclodiene-specific antibody which remains bound to the immobilized antigen on the reaction plate. Limited color in the microtiter reaction well indicates a high concentration of antigen in the sample.

The utility of such a reaction system is dependent on the surface binding of the antigenic hapten-protein complex. The sensitivity of such a binding system can be amplified by any of several means such as by coupling the enzyme reaction endpoint to a biotin-avidin complex. Optimal enzyme detection sensitivity occurs when a minimal amount of coating antigen (heptachlor-BSA) is used. The total binding capacity of the plate is large so that extra unconjugated carrier protein does not degrade binding.

Immunoassay of Organic Compounds in Food or Environmental Samples

The present invention also provides an improved method for identifying organic compounds and pesticides in the presence of other compounds found in food or environmental samples. The method is contemplated to be useful for the sensitive detection of organic compounds, pesticides and their metabolites in samples by their specific binding affinity to monoclonal antibodies which are fixed to a surface.

It is necessary to modify the isolation conditions when nonpolar compounds, non-electrolytic compounds which generally consist of carbon or nitrogen, with or without other elements, are to be assayed by a specific monoclonal antibody in a polar or electrolytic reaction medium of the immunoassay.

Evaluation of organic compounds or pesticide contamination of samples requires preliminary sample preparation to remove other organic material which may interfere with the specific antibody immunoassay. Pesticides tend to concentrate in fat and this fat may interfere with the detection immunoassay. Fat can be removed by rendering of the tissue with heating to 110° C. for 30 minutes and extraction of the rendered fat with activated resin, such as silica gel, alumina, C-18 reverse phase resin or Florisil, which is activated magnesium silicates, preferably Florisil, followed by a resuspension of the sample in a polar-non-polar solvent mixture for immunoassay.

Food or tissue samples are prepared for assay by heating and dissolving the rendered fat in organic solvent. Assay samples from soft samples, such as soils, grains and muscle tissue are ground in organic solvent, such as hexane and subjected to column fractionation. Muscle tissue of fish and other lean animals is homogenized in organic solvent, and milk is simply extracted with an organic solvent, preferably hexane. The hexane-extracted fat fraction is applied to an activated glass column in which the resin is used in a ratio of 50–100 times the weight of the fat sample. The fat soluble components are eluted from an activated glass column, preferably a Florisil column, which is activated magnesium silica, with organic solvent such as hexane and the solvent evaporated under a stream of inert gas ($N_2$@30° C.). The residues are then resuspended in alcohol, preferably 100% methanol and subsequently diluted to 25% methanol prior to assay with cyclodiene-specific monoclonal antibodies of the invention. Other sample preparation techniques, when used for HPLC or GC analysis, use a smaller amount of Florisil and may leave residues which may interfere with the immunoassay.

This sample preparation method is suitable for a variety of organic compounds, including those with one or more 5 or 6 carbon ring structures. It is especially suitable for heterocyclic pesticides, their production by-products and metabolites.

A kit format of the detection system may be used for field analysis of surface wiped or extracted samples. The specific antibodies developed here can be used in a diagnostic kit for office or field testing of samples which are suspected of containing cyclodiene insecticides or metabolites of such. A card or a cup test format may be used in which the antibody is affixed to an absorbent layer, or is mixed in a permeable layer which is bound to an absorbent layer.

Isolation of Cyclodienes

The binding specificity of the described monoclonal antibodies of this invention for cyclodienes may be utilized in a binding column to selectively discriminate cyclodienes. Compounds with the norbornene structure may reversibly bind specifically to monoclonal antibodies, produced by this invention, which are fixed in a column. Differential binding of cyclodiene compounds to a column of fixed monoclonal antibody may also be used to remove, purify or concentrate these compounds. An exemplary separation method is binding and release of a compound by alteration of the ionic concentration of the column.

The following examples, presented by way of illustration, serve to explain the present invention in more detail. These examples are not to be construed as limiting the invention to the precise forms or modes disclosed. In fact, several improvements and modifications are possible. It is intended that such improvements and modifications are encompassed by the appended claims.

EXAMPLES

1. Synthesis of Cyclodiene Hapten and Immunogen

The cyclodiene compound, heptachlor, is a small molecule, which by itself has limited immunogenicity. A hapten is formed by condensation of hexachloropentadiene and cyclopentadiene to develop an intermediate, chlordene, and oxidation of the intermediate to form 1-hydroxychlordene by the method of Buchel et al. Chem. Ber. 99:405 (1966).

The 1-hydroxychlordene hapten is rendered immunogenic by coupling it to an immunogenic carrier protein through a succinate moiety. The conjugated hapten-protein elicits formation of an antibody which will recognize several different cyclodienes.

In particular, the condensation reaction is a Dieis-Alder addition of hexachlorocyclopentadiene and cyclopentadiene to yield 4,5,6,7,8,8,-hexachloro-3a,4,7,7a-tetrahydro-4,7-methanoindene which is oxidized with selenium dioxide to 1-exo-hydroxy-4,5,6,7,8,8-hexachloro-3a,4,7,7,a-tetrahydro-4,7-methanoindene. The composition of the heptachlor-hapten was verified by physical analysis.

The hapten was rendered immunogenic by coupling to an immunogenic carrier protein through a succinate moiety. In particular, 1-exo-hydroxy-4,5,6,7,8,8-hexachloro-3a, 4,7,7a-tetrahydro-4,7-methanoindene was treated with succinic anhydride in pyridine. The resulting solution was evaporated in vacuo, dissolved in 5% aqueous sodium bicarbonate, washed with chloroform, and the aqueous solution was acidified with concentrated hydrochloric acid to give the crude hemisuccinate. The crude material was conjugated to bovine serum albumin and keyhole limpet hemocyanin by a N-hydroxysuccinimide procedure such as that described by Lauer et al. Experientia 30: 558 (1974), which is incorporated by reference.

The hapten-protein conjugates used for immunization were produced by conjugation of the 1-hydroxychlordene hemisuccinate to keyhole limpet hemocyanin (KLH) to form (heptachlor-KLH), and to bovine serum albumin (BSA) to form (heptachlor-BSA) using acid anhydride intermediate which readily couples to the free amine groups of the protein. KLH conjugates were used for immunization of animals and BSA conjugates were used for ELISA screening of hybridoma clones.

2. Immunization of Animals with Antigen

Antibodies to cyclodienes were raised by repeated injection of a mammal, in the preferred mode, mice, with a heptachlor-keyhole limpet hemocyanin conjugate (heptachlor-KLH). In the preferred method, the heptachlor-keyhole limpet hemocyanin conjugate, preferably 1-hydroxychlordene-KLH, made as described above, was used to immunize 6-month old BALB/cBkl mice by repeated intraperitoneal injections, preferably three, of 50 μg heptachlor-KLH conjugate, mixed with Ribi adjuvant. In the preferred mode, the mice received a single injection every other week for three injections.

3. Production of Hybridomas

Four days prior to lymphocyte fusion, mouse hapten-specific serum titer was boosted with an intrasplenic injection of 100 ug cyclodiene-bovine serum albumin conjugate, preferably 1-hydroxychlordene-BSA conjugate in sterile saline. Hybridoma fusions, of lymphocytes to SP2/0 myeloma cells were made by standard methods such as those described by Bigbee, W. L. et al. Molecular Immunology 20: 1353–1362 (1983)), and grown under suitable conditions such as those described by Stanker et al. (1986) (J. Immunol. 136: 4174–4180). The papers describing the methods of Bigbee et al. and Stanker et al. are incorporated by reference. Fusion is not limited to the use of SP2/0 myeloma cells and the use of other immortally reproducing mammalian cells is contemplated to be within the scope of this invention. Following fusion, hybridomas were screened in a direct binding ELISA for the ability of the antibodies which they produced to recognize the appropriate BSA-hapten conjugates.

4. Screening for Cyclodiene Specific Antibodies by Direct Binding ELISA Assays

A direct binding ELISA assay, a modification of the method of Stanker et al. (1986) (J. Immunol. 136: 4174–4180), was used to screen against a variety of heptachlor and heptachlor-related antigens for antibodies to cyclodienes in the culture fluids of growing hybridomas.

The 96-well Immulon-II microtiter plates (Dynatech Laboratories, Alexandria, Va.) were coated with a cyclodiene hapten-protein complex, preferably 1-hydroxychlordene-bovine serum albumin complex in the amount of about 0.002–0.5 ug per well, preferably about 0.2 ug per well, in carbonate-bicarbonate buffer (pH 9) for 18 hours at 4° C., blocked for 1 hour at room temperature with a 1% solution of ovalbumin, and then incubated for 1 hour at 37° C. with the hybridoma supernatants. The plates were carefully washed with a solution of surfactant compounds selected from a variety of surfactant agents in a concentration of 0.0001–0.1%, especially preferred was 0.05% Tween-20 TM (Polyoxethylenesorbitan Monolaurate) in water.

For visualization of the binding of the cyclodiene-specific antibody, a detectable endpoint reaction was used such as a fluorometric endpoint or the colorimetric endpoint of an enzymatic reaction. In the preferred example, mouse peroxidase, conjugated with goat anti-mouse antiserum (United States Biochemicals, Cleveland, Ohio), was diluted 1:500 in conjugate dilution buffer (0.005M, 0.075N NaCl, 0.001% Tween-20, pH 7.2), and was added to each well. Following a second one-hour incubation at 37° C., the plates were washed again and the substrate, 2,2 amino-di-3-ethylbenzthiazoline sulfonic acid (ABTS), added.

Absorbance measurements at 405 nm were taken as a function of time and the resulting data were transferred to a Macintosh computer and subsequently analyzed by a procedure such as that using the "Cyberdoma" ELISA software described by Slezak et al. (1983) (J. Immunol. Methods 65: 83–95). Presence of enzyme-catalyzed color reaction which was indicative of the presence of mouse antibody bound in the wells.

Hybridoma cells from wells showing a positive response in the ELISA screen were expanded and subcloned twice by limiting dilution to ensure their monoclonal origin. Ascites fluid was prepared in irradiated mice according to Stanker et al. (1986) (J. Immunol. Methods 136: 4174–4180), and the monoclonal antibodies purified from the ascites by a method such as hydroxylapatite chromatography as described by (Stanker et al. (1985) *J. Immunol. Methods* 76: 157-169), or by protein G affinity purification reagent as described by Pharmacia, the manufacturer of the reagent. Isotype determination was done by ELISA using mouse heavy- and light-chain specific antisera (Southern Biotechnology Assoc., Birmingham, Ala.).

Hybridomas from the fusions were cultured in 30, 96-well microculture dishes. Approximately 500 wells were observed to be secreting antibody that recognized the antigen heptachlor-BSA conjugate, but not the BSA itself. Those cells showing the strongest response and specificity (approximately 100) were expanded and tested against heptachlor-BSA, heptachlor-KLH, BSA and KLH. Antibody that recognized both hapten conjugates, but not either carrier protein, was observed in 39 wells. These were evaluated for their ability to recognize unconjugated heptachlor and heptachlor epoxide in a competition ELISA. Antibodies from only two of the hybridomas recognized the unconjugated compounds. The hybridoma which produced antibody with the highest relative affinity was named Hept-2.

Isotype of the monoclonal antibody produced by Hept-2 was determined to be $IgG_{2a}$ kappa light chain by direct-binding ELISA with isotype-specific antisera (Southern Biotech, Mobile, Ala.).

5. Assessment of Cyclodienes by Competition Enzyme-linked Immunoabsorbent Assays A competition enzyme-linked immunosorbent assay (c-ELISA) was developed to quantify heptachlor standards in solution and to assess the specificity of the antibodies for various cyclodienes and derivatives. Any of several coating antigens were used, however, preliminary work to optimize the sensitivity of the assay showed greatly improved sensitivity if heptachlor-bovine serum albumin was used. Microtiter plates were coated with 0.025 µg/well heptachlor-BSA and blocked with 300 µl of assay buffer per well for 1 hour at room temperature. The blocking solution was discarded.

In the competition ELISA, the competitors of antibody binding were dissolved in methanol and were added to assay buffer. Competitor was added so that each well contained 100 µl of competitor in a 50% methanol-assay buffer solution. An equal volume of assay buffer containing monoclonal antibody was added such that there was a final concentration of 100–200 ng antibody/well in a 25% methanol solution in assay buffer comprising antibody and competitor. These antibodies can tolerate up to 40% methanol with only minimal loss of activity. Peroxidase-conjugated goat anti-mouse IgG antibody was added. The plates were incubated for one hour at room temperature and the endpoint assessed by observation of the color change of 2,2,azino-di-3-ethylbenzthiozoline sulfonic acid (ABTS) substrate actuated by alkaline phosphatase conjugated to goat anti-mouse antibody.

Because the sensitivity of c-ELISA's can be influenced by both the amount of specific anti-hapten antibody used and the amount of immobilized binding antigen, both of these parameters were optimized. In the preferred method, the amount of antigen used to coat the microtiter plates was varied from 0.005 to 10 µg/well, with 0.025 ug/well being more preferred. Antigen was absorbed onto the wells overnight by evaporation from the antigen dissolved in distilled water at 37° C. Maximal sensitivity of the assay system was observed when the binding antigen was allowed to evaporate onto the wells.

To detect a limited quantity of coating antigen, however, the signal must be additionally amplified. Any of several enzyme-directed signal amplification systems were suitable. A preferred method of amplification of the enzyme-catalyzed optically-detected signal, when run with low background levels of plated antigen, is with an avidin-peroxidase/biotin-anti-mouse immunoglobulin system. The avidin-peroxidase/biotin-anti-mouse immunoglobulin system was used as the biotin can be easily coupled to antibodies or enzymes without loss of activity. Because of the exceptionally high binding affinity, avidin ($10^{15}$/M) forms bridging complexes between biotinylated molecules. Both the specific-binding monoclonal antibody and the peroxidase-enzyme indicator system are bound to biotin. Linkage of the biotin molecules with avidin complexes the indicator molecules and increases detection signal.

Cyclodiene specific antibody was conjugated to biotin by standard methods, such as that described by P. Tijssen in Chapter 3 of "Practice and Theory of Enzyme Immunoassays" (R. H. Burdon and P. H. Van Knippenberg, Eds., Elsevier, Amsterdam (1985)). Biotinylated-N-hydroxy succinimide (BNHS) ester was reacted with the cyclodiene-specific antibodies to make the biotinylated immunoreactants. In a preferred method, cyclodiene-specific antibody was identified by the binding of a biotinylated anti-mouse IgG immunoglobulin to the antibody, and using biotinylated peroxidase, Vectastain (Vector Laboratories, Burlingame, Calif.) for bridging to the avidin-biotin amplification complex.

The antibody of the hybridoma Hept-2 was titrated against immobilized antigen (0.025 µg antibody/well) in a direct binding ELISA. When the antibody of the hybridoma Hept-2 was used at a concentration of 0.02 µg/well, the level used in subsequent cELISA's, approximately 50% of the plateau activity was reached. In the preferred method, Tween-20 TM, in the concentration range of about 0.0001–0.1%, preferably a concentration of 0.01%, was routinely used 0.2 ml of assay buffer.

Figure 4:
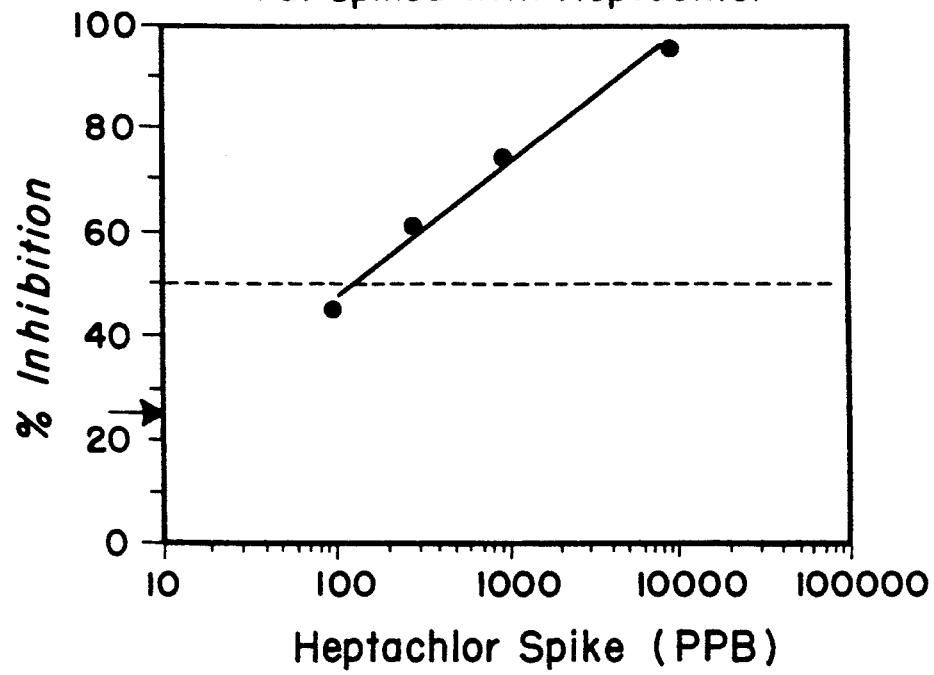
FIG. 4 shows competition ELISA data which demonstrates detection of added heptachlor in beef fat samples by monoclonal antibody from hybridoma Hept-2.

The competition ELISA data was normalized by using the optical density of wells in which antibody was bound to the solid phase antigen (heptachlor-BSA) in the absence of any competitor as the defined value of 100% activity. The test wells, each containing different amounts of competitor, were normalized to the 100% activity wells. Percent inhibition was calculated by subtracting the normalized percent activity from 100. FIG. 4 shows competition ELISA data for the monoclonal antibody from hybridoma Hept-2 when reacted with heptachlor. The $I_{50}$ for heptachlor is 2-4 ng/well.

Figure 3:
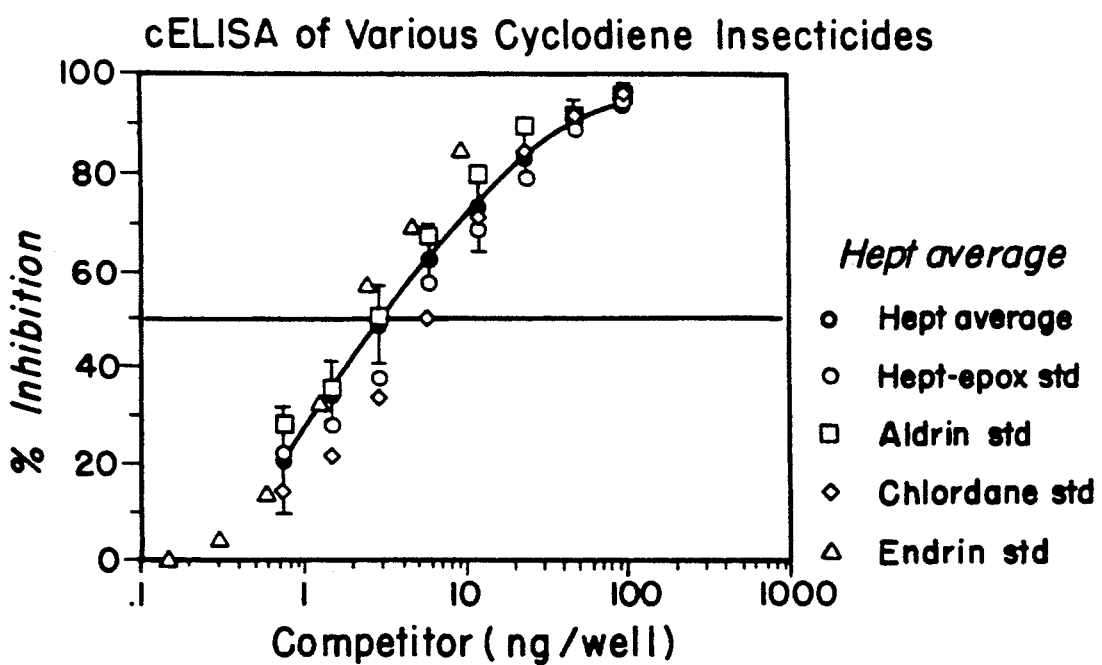
FIG. 3 shows competition ELISA data for monoclonal antibody from Hept-2 when reacted with competitors: heptachlor, (closed circle); heptachlor epoxide, (open circle); aldrin, (open square); chlordane, (open diamond); and endrin, (open triangle).

FIG. 3 shows competition ELISA data for monoclonal antibody from hybridoma Hept-2 when reacted respectively with heptachlor, heptachlor epoxide, aldrin, chlordane, and endrin, as competitors. The $I_{50}$ values observed for these competitors were all in the range of 1-10 ng/well. Replicate assays generally had less than 10% variation. A smaller $I_{50}$ value indicates a greater relative affinity of the antibody for the compound. $I_{50}$ values were estimated graphically from competition ELISA data. Table 1 represents the cross-reactivity of the monoclonal antibody from hybridoma Hept-2 with various cyclic organic compounds including (with 100% reactivity defined as the activity to heptachlor): heptachlor (100); heptachlor epoxide (100);

chlordane (75); aldrin (100): endrin (150); dieldrin (300); endosulfan(mix) (173); alpha-endosulfan (43); beta-endosulfan (250); endosulfan sulfate (182); toxaphene (100); Lindane (BHC)(mixed isomers) (7.3); and Kepone ® (5). The values listed in Table 1 represent the averages from at least two independent assays.

6. preparation of Food and Environmental Samples for Immunoassay

Samples from food or environmental sources are prepared for specific immunoassay by isolation and treatment of the lipid fraction which may contain organic or pesticide materials. Assay material from soft samples such as soils, grains and muscle tissue is ground in organic solvent, such as hexane, and subjected to column fractionation. The lipid portion of a milk sample is in the low density cream which is assayed for presence of cyclodiene contaminants.

Meat samples which contain structured fat and epithelial tissue are heated to render any fat. In the preferred method, samples are heated to 80°–150° C. for 60 minutes, a temperature of 100° C. being more preferred. A tissue sample is supported by silicanized glass wool during the rendering process. The heated samples are dissolved in organic solvent, preferably hexane at a ratio of 0.1 g of rendered fat in the sample to 1 ml of hexane.

The hexane solubilized fat of any meat, soft tissue or milk sample is applied to a previously washed 5–10 gm Florisil (Baker or Fisher Scientific, Co.) column and eluted with an excess of hexane. In the preferred mode, the volume of the Florisil column is at least ten times the volume of the hexane-fat mixture. In the preferred mode, at least 20 ml of hexane is used to elute the Florisil column. The sample eluate is dried under a stream of inert gas at room temperature, preferably $N_2$ at 30° C.

The Florisil column used for sample clean-up is prepared by activation of the gel to remove water and deactivated by addition of a defined amount of water back to the silica gel. In the preferred mode, the Florisil is activated by heating, at 650° C. overnight, and then stored at 130° C. in an open container. For optimal results, the resin is selectively deactivated by addition of water back to the desiccated resin by addition with an atomizer with shaking between water additions. The preferred deactivated resin contains 7% w/w water. The deactivated resin is allowed to sit overnight before use, and can be stored in a closed container at room temperature.

The Florisil column used for cyclodiene samples is prepared by addition of 5–10 grams of deactivated Florisil to a 10 ml disposable syringe barrel or a disposable column (Bio-Rad, Richmond Calif.) which has been plugged with a sandwich of glass wool formed between two glass fiber filters. The Florisil column is washed immediately prior to use with 10 ml of solvent, preferably hexane.

Samples eluted from the Florisil column are subsequently assayed by the cELISA assay described above. Hexane-extracted sample residues, which are dried down under a stream of inert gas, are resuspended in 100% methanol and diluted to 25% methanol with the aqueous assay buffer.

7. Assay of Cyclodienes in Food Samples

Antibodies produced by the above method may be used in a testing screen to identify the presence of cyclodienes in foods or environmental samples when prepared by the above method. The antibodies described can be used to distinguish the presence of the most commonly known cyclodiene insecticides.

The data herein presented indicate that the antibodies developed by the described method are suitable for detection of cyclodienes in samples from beef fat, which have been spiked with 10,000 and 100 ppb of the cyclodiene, heptachlor (FIG. 4). Good correlation was found between the estimated and measured levels of cyclodienes in all spiked samples which contained more than 50 ppb. The expected level of cyclodiene contamination correlates well with that observed in spiked samples, when a greater than 95% recovery was assumed.

Figure 5:
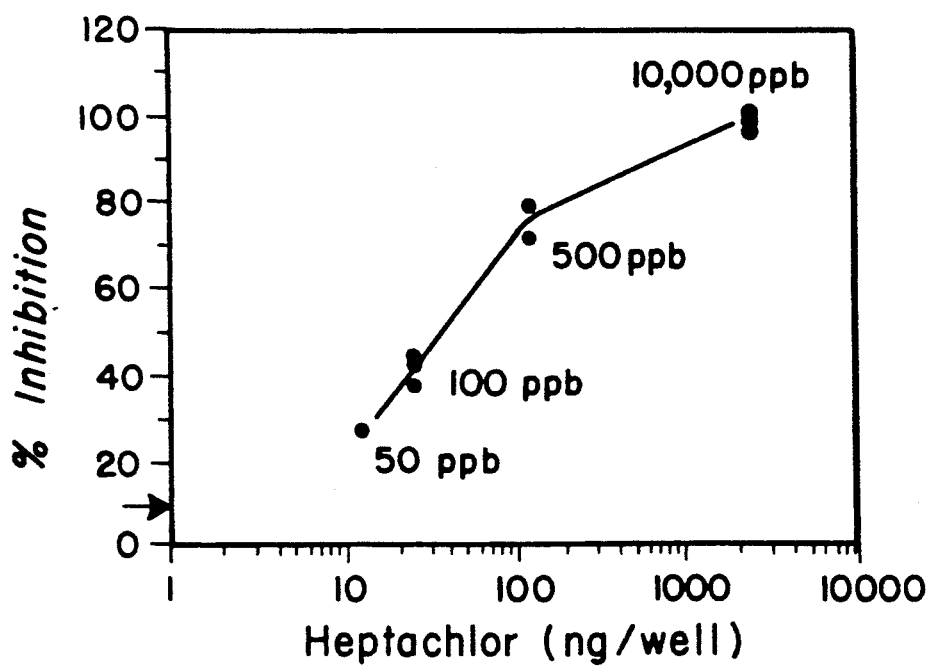
FIG. 5 shows competition ELISA data which demonstrates detection of heptachlor in spiked samples of fish muscle by monoclonal antibody from hybridoma Hept-2.

FIG. 5 demonstrates the detectable amounts of heptachlor when heptachlor-spiked fish muscle is extracted and assayed with monoclonal antibody from the hybridoma Hept-2.

Figure 6:
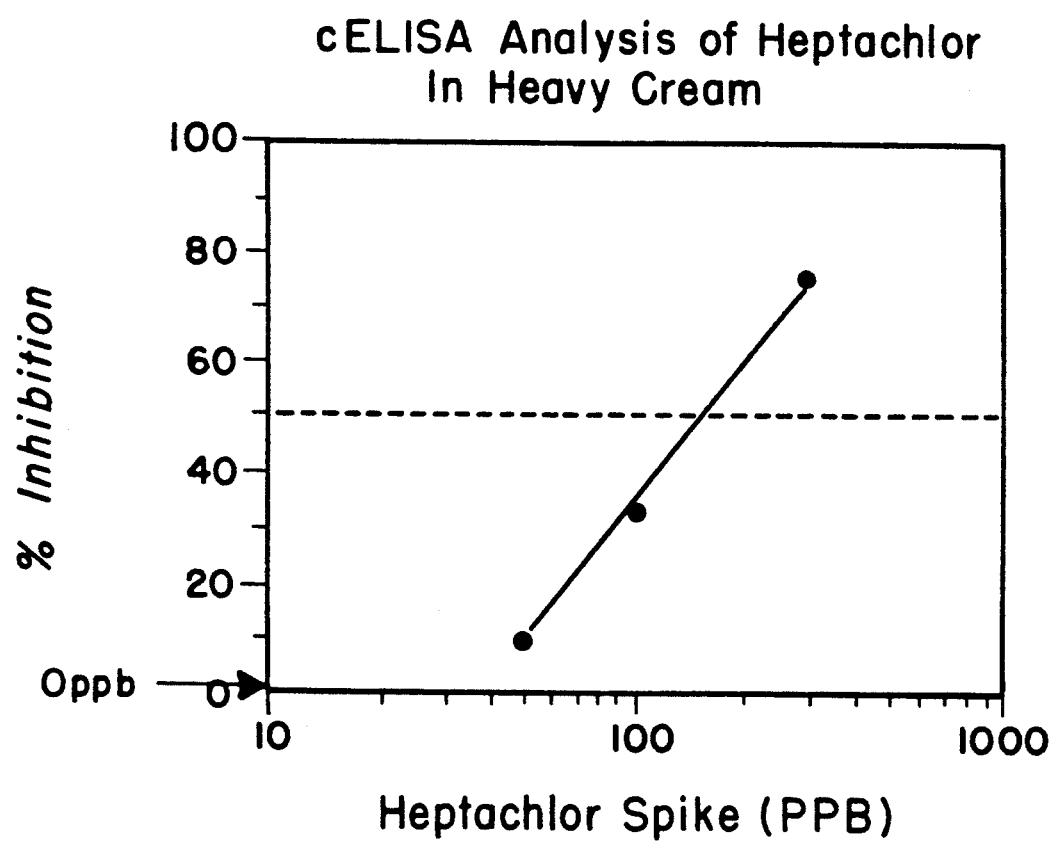
FIG. 6 shows competition ELISA data which demonstrates detection of heptachlor in spiked samples of heavy cream by monoclonal antibody from hybridoma Hept-2.

FIG. 6 shows detection of heptachlor in heptachlor-spiked samples of cream which are extracted with hexane, bound to and extracted from a Florisil column with hexane, and assayed with monoclonal antibody from hybridoma Hept-2.

8. Methods for Purification of Cyclodienes

The antibodies herein developed are covalently bound to a column and used to extract cyclodienes from samples of foods or environmental materials which are eluted through the column. Subsequent elution and repeated extraction are used to concentrate cyclodienes and metabolites for further evaluation.

9. Kit for Field Detection of Cyclodienes

The monoclonal antibodies described herein, when placed in a kit format, are used for a rapid, field-portable assay for the detection of cyclodiene insecticide residues. A kit assay for field inspectors uses cyclodiene-specific antibodies including those described herein and does not require use of sophisticated optical systems for detection of antibody binding reaction endpoints.

The kit contains cyclodiene-specific monoclonal antibodies which are immobilized on the surface of a reaction vessel or plate. The immobilization surface is precoated on a disposable tube or on a porous surface card, where the antibodies contact or overlay an absorbant material. Cyclodiene-specific monoclonal antibodies are immobilized with a protein A bridge or similar protein binding complex. This binding agent is selected to be of a sensitivity which does not interfere with the cyclodiene binding of the specific monoclonal antibody.

The indicator enzyme-conjugated hapten, used as the reporter molecule, is selected for optimal binding to and release from the surface bound cyclodiene-specific antibody. Indicator enzyme bound to one of several antigen analogs functions to bind to and release from the surface-bound antibody, with the indicator enzyme-heptachlor antigen complex, especially preferred. The enzyme-antigen conjugate is preloaded on the antibody prior to the addition of test sample, or known standard samples, or it is applied concurrently with the test sample. The indicator enzyme-antigen conjugate and the test sample and/or standard solutions are then allowed to compete for antibody-binding sites. In a preferred method, indicator enzyme antigen conjugate is preloaded. When test samples are added which contain cyclodienes, the cyclodienes compete with the indicator enzyme-conjugated hapten for a binding position on the immobilized antibody. Substrate is added which reacts with the indicator enzyme which remains bound to the immobilized antibody. Absorbance measurements of the color change of the substrate are used to quantify the amount of indicator enzyme-conjugated hapten displaced by the test sample.

The kit would also provide a prepackaged sample-collecting absorbant pad, which contains organic solvent for solubilization of the test sample from exposed environmental surfaces.

The above-described examples show that monoclonal antibodies produced by the hybridomas made as described, as exemplified by the monoclonal antibody of hybridoma Hept-2, are highly specific to cytodiene insecticides with the cyclopentadiene or dicyclopentadiene structure, and more particularly to those with the norbornene structure, and are able to distinguish compounds with similar binding activities. Selective binding of cyclodienes to monoclonal antibodies made in this way, indicate that such monoclonal antibodies, as exemplified by monoclonal antibody from Hept-2, is used to identify, simply and conveniently, low concentrations of cyclodienes present in food or environmental samples.

The subject invention thus provides monoclonal antibodies that are able to distinguish the presence of cyclodienes. The instant invention also provides cell lines which continuously secrete these monoclonal antibodies and methods for their production. The monoclonal antibodies of the subject invention bind specifically to cyclodienes and are able to distinguish compounds containing the norbornene structure. These monoclonal antibodies are contemplated to be useful in diagnostic applications including those where recognition of cyclodiene insecticides in the presence of other materials in foods or environmental samples is desirable.

The instant invention describes a method for preparation of samples which contain lipid-soluble cyclic materials, such as those commonly found in pesticides, for assay by specific monoclonal antibody in aqueous or non-polar immunoassay.

The above embodiments were chosen and described in order to best explain the principles and the practical applications of the subject invention thereby to enable those skilled in the art to utilize the invention in various other embodiments and various modifications as are suitable for the particular use contemplated. The foregoing description of some preferred embodiments of the invention, therefore, have been presented only for purposes of description and illustration of the subject invention. It is not intended to be exhaustive or to limit the invention to the precise forms disclosed, and many modifications and variations thereof would become obvious to those skilled in the art from the teachings and disclosure herein. It is intended that the scope of the invention is best defined by the appended claims.

TABLE I

| Reactivity of Monoclonal Antibody of Hept-2 | |
|---|---|
| Compound | % Crossreactivity |
| heptachlory | 100 |
| heptachlor epoxide | 100 |
| chlordane | 75 |
| aldrin | 100 |
| endrin | 150 |
| dieldrin | 300 |
| Endosulfan (mix) | 173 |
| a-Endosulfan | 43 |
| β-Endosulfan | 250 |
| Endosulfansulfate | 182 |
| Toxaphene | 100 |
| Lindand (BHC) | 7.3 |

TABLE I-continued

| Reactivity of Monoclonal Antibody of Hept-2 | |
|---|---|
| Compound | % Crossreactivity |
| Kepone | 5 |
| hexa-Cl-cyclopentadiene | 1.6 |
| hexa-Cl-butadiene | 0.4 |
| 1,2,4-triCl-Bz | 0 |
| hexa-Cl-ethane | 0 |
| 2-Cl-naphthalene | 0 |
| 1,2-diCl-Bz | 0 |
| 1,3-diCl-Bz | 0 |
| 1,4-diCl-Bz | 0 |
| 2,5-diCl-nitroBz | 0 |
| 2,4,6-triCl-phenol | 0 |
| 2-Cl-phenol | 0 |
| 2,4-diCl-phenol | 0 |
| 2,4-DiMe-phenol | 0 |
| 2-nitro-phenol | 0 |
| 4-nitro-phenol | 0 |
| 2,4-dinitro-phenol | 0.2 |
| 4,6-dinitro-cresol | 0.14 |
| penta-Cl-phenol | 0 |
| phenol | 0 |
| 4-Cl-3-Me phenol | 0 |
| 2,4,5-triCl-phenol | 0 |
| 4,5-diCl-catecol | 0 |
| 2,4-diCl-6-nitrophenol | 0 |
| 2,2,2-tri-Cl-ethanol | 0.4 |
| DDT | 0 |
| Chlorobenzene | 0 |
| 2,4,5-triCl-phenoxyacetic acid | 0 |
| 2,4-D | 0 |

A value of 0 indicates that the cross reactivity was less than 0.06%

We claim:

1. A monoclonal antibody, produced by a cell which is a fusion product of an immortal mammalian cell and immunosensitized cell from a mammal which has been immunized with a 1-hydroxychlordene hemisuccinate hapten reacted with an immunogenic keyhole limpet hemocyanin carrier protein,
wherein said antibody is identified through screening of said antibody for its binding affinity with the analog hapten of heptachlor-bovine serum albumin and cyclodiene compound and its lack of binding affinity to aid carrier protein to demonstrate the presence of reactive sites and specific affinities for compounds of the class of cyclodienes which possess the cyclopentadiene functionality; and
wherein said antibody is a product of hybridoma Hept-2, which is deposited at the ATCC with Accession No. HB 10623.

2. A hybridoma defined as Hept-2, deposited at ATCC with Accession No. HB 10623,
produced by a fusion of an immortally reproducing mammalian cell with immunosensitized cell from a mammal which has been immunized with a 1-hydroxychlordene hemisuccinate hapten reacted with an immunogenic keyhole limpet hemocyanin carrier protein, or progeny of said hybridoma,
which hybridoma produces monoclonal antibody wherein said antibody is identified through screening of said antibody for its binding affinity with the analog hapten of heptachlor-bovine serum albumin and related cyclodiene compound and its lack of binding affinity to said carrier protein to demonstrate the presence of reactive sites which react specifically with compounds of the class of cyclodienes which possess the cyclopentadiene functionality.

3. A test kit for detection of cyclodienes which contain the norbornene structure, comprising:

(a) an absorbent layer;
(b) a monoclonal antibody defined as a product of hybridoma Hept-2, deposited at the ATCC with Accession No. HB 10623:
wherein said hybridoma is produced by a cell which is s fusion product of an immortal myeloma mammalian cell and immunosensitized spleen cell from a mammal which has been immunized with a 1-hydroxychlordene hemisuccinate hapten reacted with an immunogenic keyhole limpet hemocyanin carrier protein;
wherein said antibody is identified through screening for its binding affinity with the analog hapten of heptachlor-bovine serum albumin and related cyclodiene compounds and their lack of binding affinity to said carrier proteins to demonstrate the presence of reactive sites and specific affinities for compounds of the class of cyclodienes which possess the cyclopentadiene functionality;
(c) an indicator enzyme-hapten conjugate; and
(d) a comparative reaction standard.

* * * * *